United States Patent [19]

Frisch

[11] Patent Number: 4,892,544
[45] Date of Patent: Jan. 9, 1990

[54] METHODS FOR FORMING HOLLOW, POROUS-SURFACED ELASTOMERIC BODIES

[75] Inventor: Eldon E. Frisch, Midland, Mich.

[73] Assignee: Dow Corning Wright Corporation, Arlington, Tenn.

[21] Appl. No.: 164,700

[22] Filed: Mar. 7, 1988

[51] Int. Cl.$^4$ ............ A61F 2/06; C08J 9/26; B29C 41/02

[52] U.S. Cl. .................. 623/11; 264/49; 264/236; 264/284; 264/298; 264/301; 264/344; 604/93; 623/1; 623/66; 623/901

[58] Field of Search ............ 264/49, 284, 299, 301, 264/302, 344, 298, 236; 623/1, 11, 66, 901; 604/93

[56] References Cited

U.S. PATENT DOCUMENTS

| | | | |
|---|---|---|---|
| 2,688,139 | 9/1954 | Jardon | 3/13 |
| 2,971,221 | 2/1961 | Schoenbeck | 264/178 R X |
| 3,121,762 | 2/1964 | Hafstad et al. | 264/177 R X |
| 3,376,238 | 4/1968 | Gregorian et al. | 264/49 X |
| 3,700,380 | 10/1972 | Kitrilakis | 3/1 |
| 3,930,979 | 1/1976 | Vallance | 204/252 |
| 3,950,467 | 4/1976 | Yazawa et al. | 264/178 R X |
| 3,980,613 | 9/1976 | Bachot et al. | 264/45.3 |
| 3,992,725 | 11/1976 | Homsy | 3/1 |
| 4,003,818 | 1/1977 | Juillard et al. | 204/296 |
| 4,003,973 | 1/1977 | Kurokawa et al. | 264/178 R X |
| 4,129,470 | 12/1978 | Homsy | 156/155 |
| 4,199,864 | 4/1980 | Ashman | 433/175 |
| 4,244,689 | 1/1981 | Ashman | 433/175 |
| 4,281,669 | 8/1981 | MacGregor | 128/784 |
| 4,321,230 | 3/1982 | Hungerford | 264/178 R X |
| 4,355,426 | 10/1982 | MacGregor | 3/1.4 |
| 4,374,669 | 2/1983 | MacGregor | 75/208 R |
| 4,459,252 | 7/1984 | MacGregor | 264/46.9 |
| 4,604,762 | 8/1986 | Robinson | 623/1 |
| 4,627,836 | 9/1986 | MacGregor | 604/93 |
| 4,759,757 | 7/1988 | Pinchuk | 623/1 |

OTHER PUBLICATIONS

U.S. patent application Ser. No. 111,889, "Methods for Forming Porous-Surfaced Polymeric Bodies", filed 10-23-87.

Primary Examiner—Philip Anderson
Attorney, Agent, or Firm—Susan M. Cornwall; Allan O. Maki

[57] ABSTRACT

A method of forming hollow, porous elastomeric bodies and hollow, duo-layered elastomeric bodies wherein one layer is porous and contiguous with the other layer which is solid by (a) coating a surface of a mandrel with a coating liquid, (b) adhering a layer of water-elutable particles onto the coated mandrel surface, (c) applying a layer of fluid elastomer composition to the particle-coated mandrel surface wherein the elastomeric composition is capable of forming a water-insoluble elastomer, (d) causing said elastomeric composition to form a cohesive mass while in contact with the particle-coated mandrel surface, (e) dissolving said elutable particles from the cohesive mass with a water-based solvent, and (f) removing the cohesive mass from the mandrel. The coating liquid comprises water and may also further comprise a wetting agent and/or a sugar. The invention also relates to the method wherein the water-elutable particles are adhered to the mandrel surface by heating the mandrel surface. The method is useful for making prostheses, e.g., mammary prostheses and vascular prostheses.

20 Claims, 2 Drawing Sheets

METHODS FOR FORMING HOLLOW, POROUS-SURFACED ELASTOMERIC BODIES

BACKGROUND OF THE INVENTION

The present invention relates to methods of forming hollow, porous elastomeric bodies and hollow, duo-layered elastomeric bodies wherein one layer is porous and continuous with the other layer which is solid.

In the medical field, it has been suggested that it is advantageous for some applications to use implantable polymer-based devices having porous surfaces. For example, it has been suggested that vascular prostheses having porous surfaces on the inside aid in keeping blood clots on the surface of the vascular prosthesis and reduce the chances of having the clots break off the vascular wall, enter the bloodstream, and embolize to various parts of the body. It has also been suggested that having a porous outer surface on mammary prostheses reduces the chances of capsular contracture.

Various patents disclose methods of making porous polymeric bodies. For example, U.S. Pat. Nos. 4,604,762 and 4,459,252 disclose methods for forming porous-surfaced prostheses by mixing salt particles or other water-elutable material with an elastomeric composition, allowing the composition to harden, and removing the water-elutable material by leaching with water.

U.S. Pat. No. 4,199,864 discloses a method of fabricating a plastic implant having a porous surface by coating a mold interior with a release agent, sprinkling a layer of water-soluble crystals on the coated surface, adding an acrylic polymer and monomer mixture to fill the mold, heat curing the mixture, and, subsequently, removing the water soluble crystals by leaching. Examples of the release agent are given as mineral oil and a release agent "sold under the name 'Mar-va-foil'".

U.S. Pat. No. 3,700,380 discloses a method of forming blood handling prostheses containing microcavities by applying fibrous, particulate, or granular material such as NaCl crystals to the surface which is to contain microcavities, while the surface is soft, causing the surface to set up, and thereafter using a solvent which dissolves the particles.

SUMMARY OF THE INVENTION

In view of these methods, there remains a need for an improved method of making hollow, porous-surfaced elastomeric bodies on a mandrel, where the method (1) is relatively simple to perform with relatively few steps, (2) allows for simple control of the pore size, (3) does not require homogeneously dispersing insoluble materials in the elastomeric composition or mixing of viscous compositions, (4) does not require bonding, lamination, or using multiple solutions to make a porous and non-porous dual-layered body, (5) can utilize elastomeric dispersions or solutions, including those in organic solvent, (6) can utilize relatively low viscosity elastomeric compositions, (7) minimizes polymer entrapment of elutable particles, (8) does not require use of a mold release agent, (9) uses readily available materials, (10) can be used to form hollow bodies with a constricted opening, (11) can be used to form complex-shaped bodies, (12) can use materials safe for medical use, (13) can use elutable materials which are nontoxic in small quantities and are elutable with water, (14) permits use of reusable standard stainless steel mandrels for making, e.g., mammary prostheses, (15) requires minimal changes from current procedures for making, e.g., mammary prostheses, (16) is relatively inexpensive, (17) and can form porous bodies or bodies with non-porous and porous layers continuous with each other and of the same material.

The invention disclosed herein provides a method of making a hollow elastomeric body having a porous surface layer by (a) coating a surface of a mandrel with a coating liquid, (b) adhering a layer of water-elutable particles onto the coated mandrel surface, (c) applying a layer of fluid elastomer composition to the particle-coated mandrel surface wherein the elastomeric composition is capable of forming a water-insoluble elastomer, (d) causing the elastomeric composition to form a cohesive mass while in contact with the particle-coated mandrel surface, (e) dissolving the elutable particles from the cohesive mass with a water-based solvent, and (f) removing the cohesive mass from the mandrel, wherein steps (e) and (f) may be completed in any order. The coating liquid comprises water and may also further comprise a wetting agent and/or a sugar. The invention also relates to the method wherein the water-elutable particles are adhered to the mandrel surface by heating the mandrel surface rather than by coating the mandrel first with the coating liquid. The body made by the method of this invention may have a porous layer and a non-porous layer contiguous with the porous layer.

BRIEF DESCRIPTION OF THE DRAWINGS

The above and other objects and advantages of the present invention will become apparent to those skilled in the art upon an examination of the following description and drawings which are illustrative of the present invention.

In the Drawings.

DETAILED DESCRIPTION OF THE INVENTION

Figure 1:
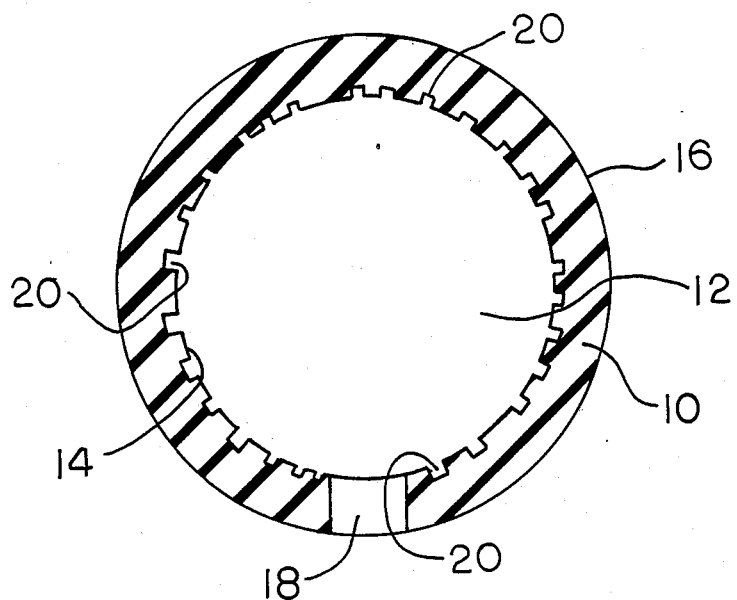
FIG. 1 is a side cross-sectional view of a hollow porous-surfaced elastomeric body made according to the method of this invention.

Briefly, the invention is a method of forming porous-surfaced polymeric bodies by adhering water-elutable particles to the outside of a mandrel, then coating the mandrel with a fluid elastomeric composition, causing the elastomeric composition to harden or set up, then dissolving the particles and removing the elastomer from the mandrel.

For this invention, there are two general techniques for adhering the water-elutable or water-soluble particles, such as salt or sugar, to the outside surface of a mandrel. The first technique involves pre-coating the surface with a coating liquid and the second technique involves heating the mandrel to a temperature to partially melt the particles. Examples of suitable coating liquids for pre-coating are water, water and wetting agent solutions, sugar-in-water solutions, and wetting agent, sugar, and water solutions. Wetting agents are employed in the coating liquid when the liquid does not uniformly wet the mandrel to the desired degree. Usually only very small amounts of wetting agents are needed and would depend on the efficiency of the particular wetting agent. The optimum concentration of a particular wetting agent can be determined through routine experimentation. Various wetting agents that are known for increasing the spreading of water on a surface may be used, including anionic, cationic, and non-ionic wetting agents. Examples of such wetting agents include soaps, such as fatty acid soaps, rosin soaps, and tall oil soaps, and synthetic detergents, such as fatty alkanol amides, sulfonated amides and amines, ethoxylated/propoxylated amines/amides, amine oxides, olefin sulfonates, alkyl aryl sulfonates, ethoxylated alcohol sulfates and sulfonates, and ether sulfates. Commercial bar soaps and dishwashing liquids have been found suitable.

Various types of sugars may be used for the sugar-in-water solutions, also. For example, sugars such as glucose, fructose, sucrose, etc., invert sugar (found in fruits and honey), and mixtures thereof are suitable sugars for this invention. The preferred concentration of sugar in the solution ranges from the minimum which allows the solution to trap the water-elutable particles to the maximum which makes the solution too thick to conveniently coat the mandrel. Generally, preferred sugar concentrations are in the range of from 5–25 weight % based on the total weight of the solution. The sugar-in-water solution is the preferred coating liquid. In some instances, it may be desirable to include additives in the sugar-in-water solution. For example, adding a wetting agent would improve the wettability of the solution, and adding an additive such as corn starch would help minimize the crystallization of the sugar and help keep the coating liquid layer smooth.

The coating liquid may be coated on the mandrel by dipping, spraying, rolling, brushing, etc. and may be placed in selected parts on the mandrel or cover the entire outer surface of the mandrel.

Once the coating liquid has been applied to the mandrel, it may be dried, however, it should not be evaporated to completion, as the water-elutable particles will not adhere to a dry, cool surface. Preferably, when using syrup and before attaching the particles, the syrup is allowed to dry enough so that it does not migrate appreciatively, yet it remains sticky. In an alternative method, the syrup is allowed to dry to a non-tacky state and then the mandrel is heated to a temperature which makes the syrup become sticky once again which allows the particles to adhere to the syrup.

The second technique of attaching the elutable particles is by heating the mandrel surface to a temperature where the particles melt partially and adhere to the mandrel when they contact the heated mandrel. This method has been found to work well when sugar is used as the elutable material because of its low melting point relative to other elutable materials, such as salt. The heating may be accomplished by an internal heating mechanism or an external heating mechanism. The temperature of the outside surface of the mandrel should be at least the melting temperature of the particles used. The particles should not melt completely in order to maintain some shape which will provide for the porous nature of the elastomeric body resulting from the method. Therefore, the mandrel should be allowed to cool after applying the particles before the particles melt completely.

Suitable water-elutable particles are those such as salt, sugar, sodium bicarbonate, polyvinylalcohol, cellulose, gelatin, and polyvinylpyrrolidone. Preferably, the particles used are salt or sugar. Optionally, additives, such as anti-caking compounds, may be added to the particles. If a solvent dispersion or solution is used as the elastomeric composition, the composition's solvent should not dissolve the water-elutable particles.

The particles may be applied to the mandrel surface by spraying, dipping, pouring, etc. the particles onto the liquid-coated or heated mandrel. Selected areas of porosity can be achieved by applying the particles to selected parts of the mandrel or the particles may be applied to the entire surface of the mandrel.

In a preferred embodiment of the invention, sugar or salt crystals are applied by dipping a syrup-coated mandrel in a fluidized bed of the crystals. The fluidized bed may simply be made by forcing substantially dry air through the screened bottom of a container which contains the crystals. The bed may be operated at a worm temperature, although not so hot as to melt the particles. The air must be substantially dry to keep the crystals from caking. Advantageously, when using a fluidized bed to coat the mandrel, the technique is fast and the resulting coating is generally uniform. Optionally, the particle-coated mandrel can be misted with water and the wetted particle-coated mandrel coated again with an additional layer of particles, and the steps repeated so that a multitude of layers of particles can be applied. Once the mandrel is coated with particles, the mandrel may be blown gently with air or other gas to remove loose particles.

Sugar and salt are available in different sizes which allows for simple control of pore size. The size range of any of the various types of particles usable in the invention may be further refined by screening the particles.

Various elastomeric compositions may be used in the method of this invention, so long as the compositions can be in a fluid form that does not dissolve the elutable particles on the mandrel surface. Furthermore, the compositions must be capable of forming a material which does not dissolve with water (which is used for dissolving the particles). Highly suitable compositions are crosslinkable compositions and thermoplastic compositions which are fluid at low enough temperatures for application to the particle-coated mandrels without significantly distorting the shape of the particles. The compositions may b solventless or in solvent. The compositions may be curable at room-temperature, or with exposure to heat, UV, or electron-beam, etc. with or without partial vacuum. The curing temperature is, at least initially, limited by the temperature that the particles will withstand before losing their shape. Once the elastomer is formed into a porous cohesive mass, generally the curing temperature may then be increased to the melt temperatures of the particles or above, as the particles are no longer needed to provide for the shape of the pores. For the method of this invention, it is preferred that compositions requiring at least mild heating be employed to avoid premature gelation of the composition prior to application to the mandrel. More than one composition may be used for making an elastomeric body of this invention so long as the compositions bond together or somehow together form a coherent mass. For example, an elastomeric body may be made of two materials, one material forming half of the body and the other material forming the other half. A body may also be made of two materials wherein the inner surface of the body is of one material and the outer surface is of the other material. This latter example would be formed by coating the mandrel first with one material and subsequently coating with another material.

Suitable elastomeric compositions include silicone and fluorosilicone compositions. Suitable silicone compositions that may be used in the method include, for example, elastomeric compositions which cure via ≡SiH to CH$_2$≡ addition, in the presence of a catalyst, such as a platinum catalyst. This addition reaction, which is well-known in the silicone art, may be room temperature or heat curing. Preferably, the composition is diluted in a suitable solvent, e.g. 1,1,1 trichloroethane, to prolong curing of the composition and to obtain a desired working viscosity. Other solvents that will dissolve uncured silicone elastomer compositions would work in this invention, also. For example, hexamethyldisiloxane could be the solvent for polydimethylsiloxane compositions and di-trifluoropropyltetra-methyldisiloxane could be the solvent for fluorosilicone compositions.

Condensation curable compositions containing siloxanes having ≡SiOH radicals and cross linkers having ≡SiOR radicals, which are also well-known in the silicone art, could also be used, especially if they were sprayed on from a two-part package, wherein one part is reactive toward the other, so they are not brought into contact with one another until they are applied to the mold surface.

Viscosity of the composition applied is an important consideration. If the viscosity of the composition is too high, it will be difficult to spread over the particles and coat the mandrel. If the viscosity is too low, there will be excessive run off. Preferably, the viscosity of a silicone composition is from about 200 to about 2000 cps. as measured with a BROOKFIELD viscometer using a #1 spindle and a speed of 10 RPM's. Suitable concentrations of dispersions of silicone compositions in trichlorethane range from about 9-15 weight % silicone in 1,1,1 trichlorethane, with more preferred concentrations ranging from 9 to 10 weight % silicone.

Apply the elastomeric composition may be done by dipping, spraying, pouring, or any other technique which will not substantially disturb the particles. Typically, if a body having a porous layer and a non-porous layer is desired, the coating of the mandrel is continued at least until the surface turns from dull to shiny, indicating a smooth, non-porous outer surface. Using this invention a body can be formed which is entirely porous by coating the layer of particles only and not coating beyond the outer surface of the particles. Similarly, a body having a porous layer on only part of its surface can be formed by applying the layer of particles to only a portion of the mandrel.

To reduce air bubble formation at the mandrel/elastomer interface, several techniques are possible. Some of these techniques are, namely, (1) pre-wetting the mandrel in the dispersion solvent before coating with the dispersion, (2) immersing the mandrel in the dispersion longer for the first coat to allow the air to escape, (3) drawing a slight vacuum on the dispersion and the mandrel during coating to remove much of the air present, and (4) coating the porous mandrel by spraying.

The thickness of the elastomeric body can be controlled by the amount of composition applied to the mandrel, e.g. by the number of dips and/or the viscosity of the elastomeric composition.

The conditions for setting or curing the applied elastomeric composition are dictated by the type of composition used. In most cases, the composition needs only to be partially cured to continue with the process and dissolve the elutable particles. If the elastomeric composition is to be heat cured, the composition must be curable at temperatures mild enough so as not to significantly deform or melt the particles before the elastomeric composition is substantially set. For the above-mentioned platinum-curable silicone composition, cure temperatures of less than 150° C. are preferred. The most preferred method of curing this type of composition is to cure initially at 75° C. to remove any water and to increase the temperature 10-15° C. every hour to 150° C. to have gradual drying and minimize formation of bubbles. If the elastomer is partially cured, it may be cured to completion at any time.

Once the elastomer is at least partially set, water or mildly acidic water may be used to dissolve the water-elutable particles from the elastomer. Other water-including solvents will work, but are not necessary. The water or acidic water may be heated to improve efficiency of dissolution.

Dissolution of the particles can be done anytime after the elastomer has been at least partially set. For example, dissolution of the particles may be done while the set elastomer is still on the mandrel, after it has been removed from the mandrel, or both before and after it has been removed from the mandrel. However, it is preferred that the particles are at least partially dissolved before removing the elastomer from the mandrel.

To dissolve the particles, the particles are merely exposed to the water-based solvent. In most cases, there is an opening in the elastomer body where the handle for the mandrel is positioned which provides the location where the water enters between the elastomer and the mandrel to dissolve the particles. Water may also be injected through the silicone elastomer wall. Where the elastomer is porous throughout, water may enter through the pores, also. However the dissolution is carried out, it is best that the technique be gentle so as not to disrupt the pores.

The technique of dissolving the particles before removal of the set elastomer from the mandrel has the advantage that it does not need a mold release material between the elastomer and the mandrel. This easy removal and the elasticity of the bodies formed enables the formation of hollow elastomeric bodies having a constricted opening and/or complex shapes. Bodies with constricted openings would be formed on mandrels by leaving uncoated an area which is smaller than the side of the mandrel on which the area is located, e.g. the position where a handle or support is attached. Once the elastomer is set and the particles dissolved, the elastomeric body is stretched off the mandrel, rolling the elastomeric body, if desired. Complex shapes may be made, since the elastomeric body is stretchable over contours and is easily removed due the prior removal of the particles. These hollow bodies may then be inverted to move the porous surface to the outside of the body, if desired.

Once the elastomeric body is removed, further steps may be taken to ensure that substantially all of the particles have been dissolved by using various leaching techniques that are known in the art. To completely dissolve salt or sugar particles from a silicone elastomer body, the elastomer should be soaked in a water-based solvent for several hours.

The porous surface may be further treated, as desired, e.g. to make the surface hydrophilic, and coatings, such as barrier coats, may be applied to any non-porous surface of the elastomeric body.

The methods of the invention are useful for making elastomeric bodies to be used in making mammary prostheses, tissue expanders, drug-releasing implants, or blood storage bags or tubular bodies, such as vascular prostheses.

Referring to the Drawings, FIG. 1 depicts an elastomeric body made according to the method of this invention. In this figure, elastomeric shell 10 has cavity 12, porous inner surface 14, smooth outer surface 16, and opening 18. Inner surface 14 has pores 20 randomly positioned therein.

Figure 2A:
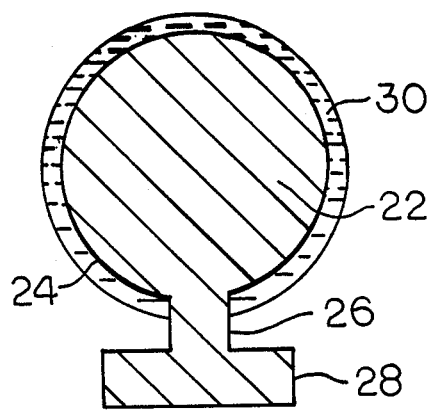
FIG. 2A–2E shows the steps of a process for forming hollow, porous-surfaced elastomeric bodies according to this invention.
Figure 2B:
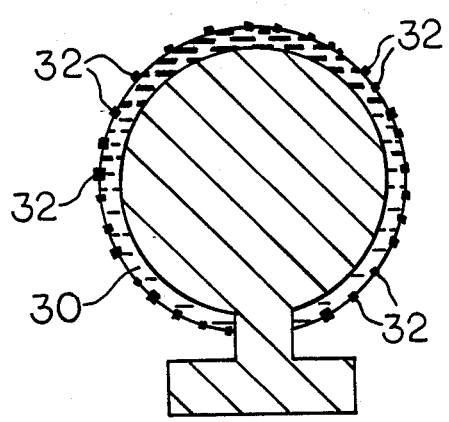
Figure 2C:
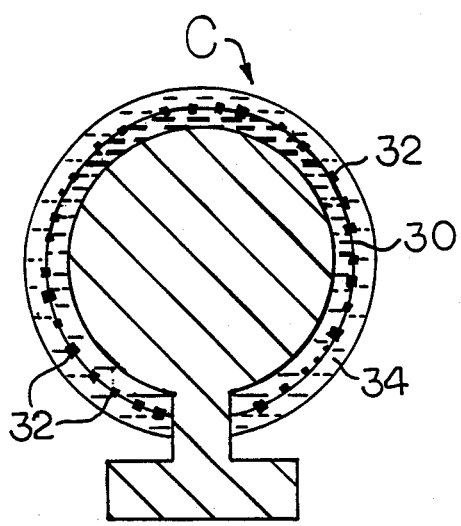
Figure 2D:
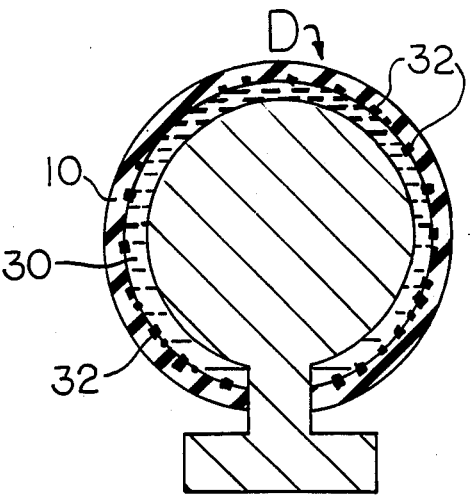
Figure 2E:
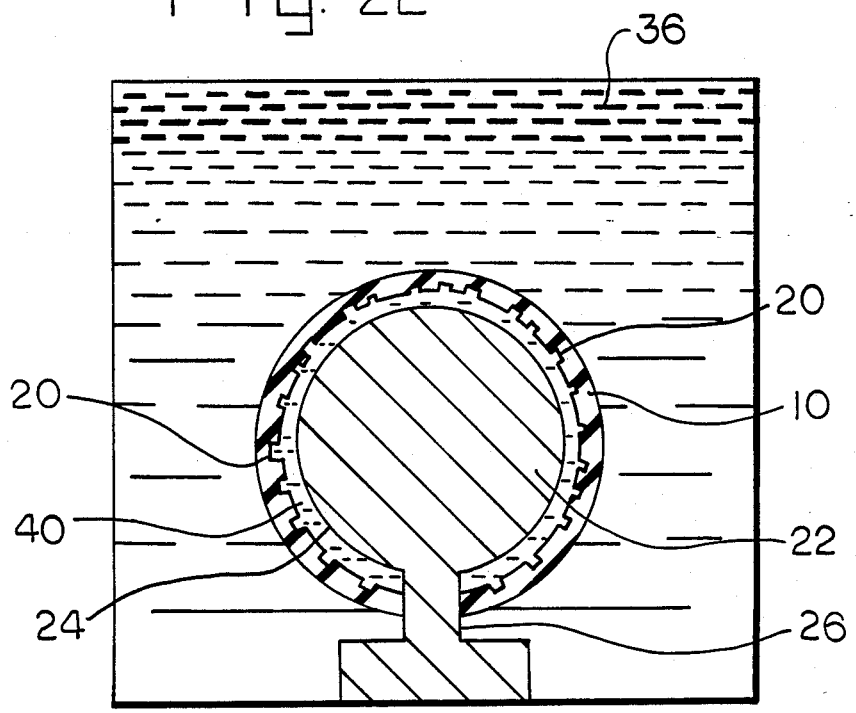

FIGS. 2A–2E shows the steps of a process according to this invention for forming hollow, porous-surfaced elastomeric bodies, such as that shown in FIG. 1. FIG. 2A shows mandrel 22 having ball top 24, stem 26, and base 28. The mandrel is formed of metal, although this is not a requirement of the invention. As a first step, as shown in FIG. 2A, ball top 24 is coated with a layer of water-containing coating liquid 30 according to this invention. For the next step, water-elutable particles 32 are applied and adhere to coating liquid 30 on ball top 24. Results of this step are shown in FIG. 2B. Particle-coated ball top 24 is then coated with a layer of fluid elastomer composition 34 according to the invention as shown in FIG. 2C. Fluid elastomer composition layer 34 is then cured as by heat or other method to form elastomeric shell 10, as shown in FIG. 2D. Elutable particles 22 are then dissolved using a water-based solvent. FIG. 2E depicts immersing coated mandrel 22 in water-based solvent 36. Upon immersion, water-based solvent 36 works its way to the surface of ball top 24 by permeation through elastomeric shell 10 and/or by entering inside elastomeric shell 10 starting at the mandrel stem 26/elastomer shell opening (created by stem 26) interface. Water-based solvent 36 dissolves elutable particles 32 and, depending on the type of water-containing coating liquid 30 used (e.g. honey), solvent 36 could dissolve liquid 30 also. Dissolution of elutable particles 32 and coating liquid 30 creates gap 40 between ball top 24 and elastomeric shell 10, shown in FIG. 2E as being filled with water-based solvent 36. At this point, mandrel 22 may be removed from the bath of water-based solvent 36, and elastomeric shell 10 may be removed from mandrel 22 by stretching or rolling elastomeric shell 10 over mandrel 22 starting at the opening in elastomeric shell 10 created by the presence of stem 26. Pores 20 remain in elastomeric shell 10 wherever water-elutable particles 32 had been embedded in elastomeric shell 10.

These and other variations of the present invention may be made which fall within the scope of the appended claims even though such variations were not specifically discussed above.

That which is claimed:

1. A method of making a hollow elastomeric body having a porous surface layer comprising
   (a) coating at least a portion of a surface of a mandrel with a coating liquid selected from the group consisting of water, water-and-wetting agent solutions, and water-an-sugar solutions
   (b) adhering a layer of water-elutable particles onto the coated mandrel surface,
   (c) applying a layer of fluid elastomer composition to the particle-coated mandrel surface, said elastomeric composition capable of forming a water-insoluble elastomer,
   (d) causing said elastomeric composition to form a cohesive mass while in contact with said particle-coated mandrel surface,
   (e) dissolving said elutable particles from said cohesive mass with a water-based solvent, and
   (f) removing said cohesive mass from said mandrel.

2. A method as claimed in claim 1 wherein dissolving step (e) is performed before removing step (f).

3. A method as claimed in claim 1 wherein dissolving step (e) is performed both before and after removing step (f).

4. A method as claimed in claim 1 wherein in step (c) said fluid elastomer composition is applied to the entire surface of the mandrel except to an area which is smaller than the side of the mandrel on which said area is located, the method thereby forming a hollow elastomeric body having a constricted opening.

5. A method as claimed in claim 1 further comprising the step of heating said mandrel after the coating step (a) and before the adhering step (b).

6. A method as claimed in claim 1 wherein said coating liquid consists of a water-and-wetting agent solution.

7. A method as claimed in claim 6 wherein said elastomeric composition is a silicone elastomer composition and the particles are selected from the group consisting of salt and sugar.

8. The method as claimed in claim 7 wherein the silicone elastomer composition is a dispersion in 1,1,1 trichloroethane.

9. A hollow elastomeric body formed by the method of claim 8.

10. A method as claimed in claim 1 wherein said coating liquid consists of a water-and-sugar solution.

11. A method as claimed in claim 10 wherein said elastomeric composition is silicone elastomer composition and the particles are selected from the group consisting of salt and sugar.

12. The method as claimed in claim 11 wherein the silicone elastomer composition is a dispersion in 1,1,1 trichloroethane.

13. A hollow elastomeric body formed by the method of claim 12.

14. A method of making a hollow elastomeric body having a porous surface layer comprising
   (a) heating at least a portion of a surface of a mandrel to at least the melting temperature of water-elutable particles,
   (b) applying a layer of water-elutable particles onto the heated mandrel surface so that the particles adhere to the mandrel without melting completely,
   (c) applying a layer of fluid elastomer composition to the particle-coated mandrel surface,
   (d) causing said elastomeric composition to form a cohesive mass while in contact with said particle-coated mandrel surface,
   (e) dissolving said elutable particles from said cohesive mass with a water-based solvent, and
   (f) removing said cohesive mass from said mandrel.

15. A method as claimed in claim 14 wherein dissolving step (e) is performed before removing step (f).

16. A method as claimed in claim 14 wherein dissolving step (e) is performed both before and after removing step (f).

17. A method as claimed in claim 14 wherein in step (c) said fluid elastomer composition is applied to the entire surface of the mandrel except to an area which is smaller than the side of the mandrel on which said area is located, the method thereby forming a hollow elastomeric body having a constricted opening.

18. A method as claimed in claim 14 wherein said elastomeric composition is a silicone elastomer composition and the particles are sugar.

19. A method as claimed in claim 18 wherein the silicone elastomer composition is a dispersion in 1,1,1 trichloroethane.

20. A hollow elastomeric body formed by the method of claim 19.